United States Patent

Weaver et al.

[11] Patent Number: 6,085,115
[45] Date of Patent: Jul. 4, 2000

[54] BIOPOTENTIAL MEASUREMENT INCLUDING ELECTROPORATION OF TISSUE SURFACE

[75] Inventors: James C. Weaver, Sudbury, Mass.; Uwe Pliquett, Grossdornberg, Germany; Rita Vanbever, Brussels, Belgium; Thiruvallur R. Gowrishankar, Waltham, Mass.; Thomas E. Zewert, Pittsburgh, Pa.

[73] Assignee: Massachusetts Institite of Technology, Cambridge, Mass.

[21] Appl. No.: 09/083,497

[22] Filed: May 22, 1998

Related U.S. Application Data

[60] Provisional application No. 60/047,389, May 22, 1997.

[51] Int. Cl.[7] .................................................. A61B 5/04
[52] U.S. Cl. ............................................................ 600/509
[58] Field of Search .................................. 600/300, 372, 600/393, 397, 508, 509, 510, 520; 609/20, 21; 607/1, 115, 133

[56] References Cited

U.S. PATENT DOCUMENTS

| | | | |
|---|---|---|---|
| 578,611 | 3/1897 | Rively | 704/21 |
| 3,078,850 | 2/1963 | Schein et al. | 128/419 |
| 3,614,955 | 10/1971 | Mirowski et al. | . |
| 3,680,544 | 8/1972 | Shinnick et al. | 128/2 R |
| 4,055,799 | 10/1977 | Coster et al. | 324/71 |
| 4,081,340 | 3/1978 | Zimmermann et al. | 204/180 |
| 4,154,668 | 5/1979 | Zimmermann et al. | 204/299 |
| 4,220,916 | 9/1980 | Zimmermann et al. | 324/71 |
| 4,411,648 | 10/1983 | Davis et al. | 604/21 |
| 4,578,168 | 3/1986 | Hofmann | 204/299 |
| 4,663,292 | 5/1987 | Wong et al. | 435/287 |
| 4,685,468 | 8/1987 | Rao | 600/393 |
| 4,695,547 | 9/1987 | Hilliard et al. | 435/173 |
| 4,764,473 | 8/1988 | Matschke et al. | 435/287 |
| 4,784,737 | 11/1988 | Ray et al. | 204/180 |
| 4,822,470 | 4/1989 | Chang | 204/299 |
| 4,955,378 | 9/1990 | Grasso | 128/421 |
| 4,979,948 | 12/1990 | Geddes et al. | 606/33 |
| 5,007,995 | 4/1991 | Takahashi et al. | 204/299 |
| 5,019,034 | 5/1991 | Weaver et al. | 604/20 |
| 5,047,007 | 9/1991 | McNichols et al. | 604/20 |
| 5,098,843 | 3/1992 | Calvin | 435/287 |
| 5,115,805 | 5/1992 | Bommannan et al. | 128/24 AA |
| 5,137,817 | 8/1992 | Busta et al. | 435/173 |
| 5,279,543 | 1/1994 | Glikfeld et al. | 604/20 |

(List continued on next page.)

FOREIGN PATENT DOCUMENTS

| 01011564 | 1/1989 | Japan . |
|---|---|---|
| 64-11564 | 1/1989 | Japan . |

OTHER PUBLICATIONS

Mir et al., "Improvement of Anticancer Electrochemotherapy", *Jr. Biochimie–Enzymologie Lab.*, Intstitut Gustave Roussy 94805 Villejuif, France.

(List continued on next page.)

*Primary Examiner*—William E. Kamm
*Attorney, Agent, or Firm*—Hamilton, Brook, Smith & Reynolds, P.C.

[57] ABSTRACT

A method for measuring biopotential of an organism includes electroporating a portion of a tissue surface of the organism. The biopotential of the organism is then measured with electrodes at the electroporated portion of the organism. The portion of the organism that is electroporated can be, for example, a skin surface of the organism. A resistance-decreasing agent, such as heparin, sodium thiosulfate, thioglycolic acid solution and dithioglycolic acid can be applied to the tissue surface to facilitate reduction in electrical resistance. Another example of a resistance-decreasing agent is a keratin-disrupting agent, such as sulforhodamine. Examples of suitable biopotential measurements include electrocardiographic, electroencephalographic, electromyographic, electrohysterographic and elctrokymographic measurements. The method decreases skin resistance to diminish unwanted electrical voltages that compete with biopotential measurements, thereby significantly improving the biopotential measurement.

30 Claims, 2 Drawing Sheets

U.S. PATENT DOCUMENTS

| | | | |
|---|---|---|---|
| 5,296,222 | 3/1994 | Petersen et al. | 424/94 |
| 5,298,017 | 3/1994 | Theeuwes et al. | 604/20 |
| 5,323,769 | 6/1994 | Bommannan et al. | 601/2 |
| 5,362,307 | 11/1994 | Guy et al. | 604/20 |
| 5,383,848 | 1/1995 | Hillman et al. | 604/20 |
| 5,389,069 | 2/1995 | Weaver | 604/21 |
| 5,445,609 | 8/1995 | Latin et al. | 604/20 |
| 5,462,520 | 10/1995 | Hofman et al. | 604/20 |
| 5,547,467 | 8/1996 | Pliquett et al. | 604/20 |
| 5,667,491 | 9/1997 | Pliquett et al. | 604/50 |
| B1 5,019,034 | 8/1995 | Weaver et al. | 604/20 |

OTHER PUBLICATIONS

Zewert et al., "Transdermal Transport of DNA Antisense Oligonucleotides by Electroporation", *Biochemical and Biophysical Research Communications* 212:286–292 (1985).

Scott et al., "Transport of Ionic Species in Skin: Contribution of Pores to the Overall Skin conductance", *Pharmaceutical Research* 10:1699–1709 (1993).

Mir et al., "Electrochemotheraphy Potentiation of Antitumour Effect of Bleomycin by Local Electric Pulses", *Eur. F. Cancer* 27 (1):68–72 (1991).

Okino et al., "Effects of a High–Voltage Electrical Impulse and an Anticancer Drug on In Vivo Growing Tumors", *Jpn. J. Cancer Res.* 78(12):1319–1321 (1987).

Heroux et al., "Assessment of Trauma in tissues by Electrica Impedance Measurements", *Electromagnetics in Biology and Medicine*, pp. 215–221 (1991).

Bhatt et al., "Rhabdomyolysis due to Pulsed Electric Fields" *Plastic and Reconstructive Surgery* 86 (1):1–11 (1990).

Heller et al., "Transfer of Human Membrane Surface Components by Incorporating Human Cells into Intact Animal Tissue by Cell Tissue Electrofusion In Vivo", *Biochimica et Biophysica Acto* 1024:185–188 (1990).

Titomirov et al., "In Vivo Electroporation and Stable Transformation of Skin Cells of Newborn Mice By Plasmid DNA", *Biochimica et Biophysica Acta.* 1088:131–134 (1991).

Okino, et al., *Journal of Japan Soc. For Cancer Therapy* 22(8):337 (1987).

Kanesda, et al., *Journal of Japan Soc. For Cancer Therapy* 22(8):338 (1987).

Okino et al., *Japan Journal of Cancert Research* 46:420 (1987).

Weaver, "Electroporation: A General Phenomenon for Manipulating Cells and Tissues", *Journal of Cellular Biochemistry* 51:426–435 (1993).

Prausnitz et al., "Electroporation of mammalian skin: A mechanism to enhance transdermal drug delivery", *Proc. Natl. Acad. Sci. USA* 90:10504–10508 (1993).

Prausnitz et al., "Methods for in Vivo Tissue Electroporation Using Surface Electrodes", *Academic Press, Inc. Drug Delivery* 1:125–131 (1993).

Bergan et al., "Electroporation enhances c–myc antisense oligodeoxynucleotide efficacy", *Nucleic Acids Research* 21(15):3567–3573 (1993).

Zewert et al., "Transdermal Transport DNA Antisense Oligonucleotides by Electroporation", *Biochemical and Biophysical Research Comm.* 212(2):286–292 (1995).

Zimmerman et al., "Effects of External Electrical Fields on Cell Membranes", *Bioelectrochemistry and Bioenergetics* 3:58–83 (1976).

Tamada et al., "Measurement of Glucose in Diabetic Subjects Using Noninvasive Transdermal Extraction", *Nature Medicine* 1:1198–1202 (1995).

Dinh e tal., "Upper and Lower Limits of Human Skin Electrical Resistance in Iontophoresis", *American Institute of Chemical Engineers Joural* 39(12):2011–2018 (1993).

Pliquett et al., "Imaginig of Fluorescent Molecules and Small Ion Transport Through Human Stratum Corneum During High–Voltage Pulsing: Localized Transport Regions are Involved", *J. Biophysical Chemistry* 58:185–204 (1996).

Pliquett et al., "Changes in the Passive Electrical Properties of Human Stratum Corneum Due to Electroporation", *Biochemica et Biophysica Acta* 1239:111–121 (1995).

Edwards et al., "Analysis of Enhanced Transdermal Transport by Skin Electroporation", *Journal of Controlled Release* 34:211–221 (1995).

BIOPOTENTIAL MEASUREMENT INCLUDING ELECTROPORATION OF TISSUE SURFACE

RELATED APPLICATION

This application claims the benefit of U.S. Provisional Application No. 60/047,389, filed May 22, 1997, now abandoned, the contents of which are incorporated herein by reference in their entirety.

GOVERNMENT SUPPORT

This invention was made with Government support under Grant Number NIH-5R01-GM34077, awarded by the National Institutes of Health, and Grant Number DAAL03-90-G-0128, awarded by the Department of the Army. The Government has certain rights in the invention.

BACKGROUND OF THE INVENTION

Biopotential measurements, also known as bioelectric potential measurements, and other electrical measurements at the surface of the skin of a living organism are often degraded by undesired electrical noise, electrical pickup and motion artifact, which involve potentials which compete with the desired biopotential measurement. For example, electrocardiogram (EKG) measurements are widely used, but in situations such as exercise there is considerable tissue movement, and this causes competing, undesired voltages. In general, this type of measurement problem is most difficult when the resistance associated with skin is largest. Resistance-lowering techniques such as mechanical abrasion or adhesive tape stripping of stratum corneum of the skin can significantly improve the quality of such electrical measurements. However, the need to mechanically alter the skin is highly undesirable, as it can be difficult to control the degree of mechanical alteration, can cause pain and discomfort, and can lead to infection.

In the case of electroporation generally, strong electric field pulses applied to cells that cause the transmembrane voltage to exceed about 0.2 V for long (e.g. 100 ms) pulses, and about 0.5 V for short (e.g. 1 ms) pulses are well known to cause ionic and molecular transport across the cell membrane. More recently, in the case of short pulses that cause the transdermal voltage, $U_{skin}$, to exceed about 50 V, ionic and molecular transport across the stratum corneum (SC) is also greatly enhanced. In both cases, the hypothesis is that aqueous pathways ("pores") are created by the applied electrical pulses such that greatly increased ionic and molecular transport occurs because of these pores. Summaries of what is understood about electroporation can be found in the book *Guide to Electroporation and Electrofusion*, Chang et al., Eds. (Academic Press) (1992), and in the reviews Weaver and Chizmadzhev, "Electroporation," in *CRC Handbook of Biological Effects of Electromagnetic Fields, Second Edition*, C. Polk and E. Postow, Eds. (Boca Raton: CRC Press), pp. 247–274 (1996), and Weaver and Chizmadzhev, "Theory of Electroporation: A Review," *Bioelectrochem. Bioenerget.*, 41:135–160 (1996), the teachings all of which are incorporated herein in their entirety.

During a simulating pulse that causes electroporation, a large voltage exists across the biological barrier (the cell membrane in the first case; the approximately 100 lipid bilayer membranes of the SC in the case of the skin), and a greatly diminished electrical resistance occurs across that barrier. In many instances, the resistance returns to prepulse values, or nearly prepulse values, comprising "reversible electroporation." For the larger pulses, and for longer pulses, artificial planar bilayer membranes exhibit irreversible breakdown, and are destroyed, so that resistance across the site of the membrane remains at a greatly diminished value. Similarly, for the larger pulses, and for longer pulses, cell membranes remain in an open state, with a greatly diminished transmembrane resistance, and the cell is usually killed. In the case of skin, for the larger pulses, and for longer pulses, $R_{skin}$ can remain at values much smaller than the initial, prepulse values. This lack of recovery is often viewed as evidence of damage to electroporated cells, often fatal damage, in the case of the SC lack of recovery is often assumed to be undesirable, even though the SC is a dead tissue. Further, a lack of recovery means that the adjacent, viable epidermis is exposed through the persistent pathways to the external environment, i.e. some of the protective feature of the skin has been lost. Thus, against the background of artificial planar bilayer membrane electroporation and cell membrane electroporation, the use of large and/or long pulses that cause skin electroporation but with slight or essentially no recovery of $R_{skin}$ is viewed as undesirable.

SUMMARY OF THE INVENTION

This invention discloses a process for improved biopotential measurements such as the EKG (ECG, electrocardiogram) by significantly decreasing the electrical resistance across tissue through electroporation, with the key feature that the decreased resistance persists at low values for times that are long enough to carry out biopotential measurements. Although general, the invention emphasizes skin tissue, particularly the stratum corneum (SC). The decreased skin resistance diminishes unwanted electrical voltages that compete with the biopotential measurement. An important case is diminished noise due to motion artifact and any local skin potentials, thereby improving biopotential measurements such as EKG (ECG, electrocardiogram) measurements during exercise stress testing.

DETAILED DESCRIPTION OF THE INVENTION

The process of this invention involves the use of "high voltage" pulses to cause electroporation within a tissue of interest, i.e. a tissue across which a biopotential (strictly, a biopotential difference, or bioelectric potential difference) is to be measured. Electroporation is well known to cause large decreases in resistance, but usually molecular transport, not electrical resistance, is of interest. Moreover, although it is also known that larger electroporating pulses cause lessened recovery of skin resistance, this relative lack of recovery is usually regarded as a potential problem. In this invention, however, this apparently undesirable feature is sought, and exploited to improve biopotential measurements that involve currents across a tissue.

Either "electrical pulsing only" can be used, or "electrical pulsing with the addition of 'resistance-decreasing agents'" can be used. The smaller value of resistance across the tissue generally leads to less electrical noise, and therefore improved biopotential measurements that involve electrical currents that flow across the tissue. A well known case is that of high skin resistance, $R_{skin}$, contributing significant noise, including "motion artifact," to biopotential measurements such as ECG (electrocardiogram) measurements.

Figure 1:
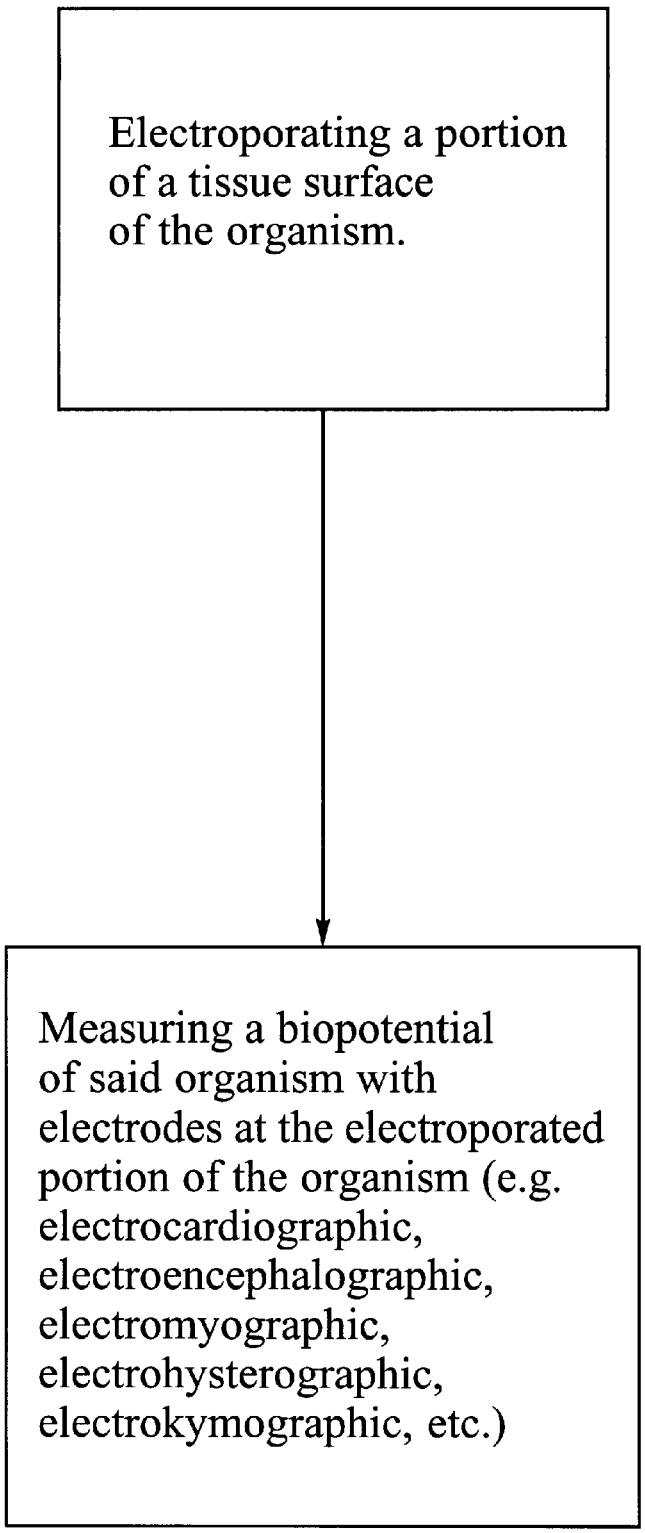
FIG. 1 is a schematic representation of the method of the invention.

The general process of this invention is represented schematically in FIG. 1 and relates to improved biopotential measurements made across a tissue. The method generally comprises several basic steps: [1] Two or more electrodes are placed in electrical connection with the tissue, so that an electrical current can be conducted across the tissue. This can, for example, be accomplished by positioning two or more electrodes close together on the surface of the tissue. Alternatively, two or more electrodes can be placed far apart on the surface of the tissue. In situations relevant to this invention, the tissue has a larger-than-desired electrical resistance when measured or computed between at least two sites. For example, in the case of the skin, the resistance between the heart, a source of currents that generate biopotentials at the surface of the skin, the resistance between the body interior and the body exterior is mainly the resistance of the skin, $R_{skin}$. The exact value of resistance depends not only on the tissue properties, but also the size and material of the electrodes used. [2] One or more electrical stimuli are applied, usually in the form of voltage pulses, but current or charge pulses can also be used. These stimuli are applied to at least one pair of electrodes such that electroporation occurs, reducing the electrical resistance such that the decreased resistance values persist for a time sufficient to carry out a desired biopotential measurement. Because of the long-lasting decreased tissue resistance, the noise (e.g. Johnson-Nyquist noise, electrical pickup, motion artifact) between said electrodes is decreased, and an improved biopotential measurement is therefore possible. [3] At least one biopotential measurement is then carried out, after the application of the electroporating stimuli (pulses), thereby improving the biopotential measurement made across the tissue. As an illustration, the process of the invention can involve placing electrodes in contact with human skin, and then applying one or more pulses sufficient to cause electroporation, so that the skin resistance, $R_{skin}$, is diminished at times of one second (1 s) or more after the last pulse. Biopotential measurements such as ECG measurements can then be made at the skin site where the long lifetime diminished $R_{skin}$ was created, with the result that there is diminished noise and motion artifact, so that the result is an improved biopotential measurement. In the case of transdermal ECG biopotential measurements, a significant improvement can be expected if $R_{skin}$ is caused to diminish to about 1000 Ω or less. The particular values of decreased resistance will depend on the type of biopotential measurement, and the magnitude of the biopotential signal in comparison to all of the noise sources.

Although this invention can be used with other tissues than skin, biopotential measurements made across the skin comprise the presently preferred embodiment. Moreover, although veterinary applications involving animal skin are envisioned, improved biopotential measurements across human skin are presently viewed as the most important.

One general method for achieving a diminished $R_{skin}$ involves applying one or more short (pulse duration of about 1 ms) pulses that cause the transdermal voltage, $U_{skin}$, to reach large values, e.g. $U_{skin}$>400 V. Alternatively, a long (pulse duration equal to or exceeding about 100 ms) pulses can be used, but in this case the transdermal voltages are smaller, e.g. $U_{skin}$>100 V. This was demonstrated in a series of experiments, which are presented in the Examples, infra.

Long lasting diminished resistance across tissue can also be achieved by using an additional step of providing resistance-decreasing agents at the surface of the tissue, such that upon electroporation the agents are transported into the skin, and the interaction of these agents with the skin then contributes to a decreased electrical resistance across the tissue. One class of resistance-decreasing agents consists of long, linear molecules that enter the electrically created aqueous pathways, and hold open cell membranes of the tissue. Examples of such molecules are heparin and dextran. This "foot-in-the-door" effect has been suggested as possibly occurring for individual cell electroporation (see Weaver, "Electroporation: A General Phenomenon for Manipulating Cells and Tissues," *J. Cellular Biochem.*, 51:426–435 (1993)), and has been inferred to occur transiently during DNA introduction into isolated cells (see Sukharev et al., "Electroporation and Electrophoretic DNA Transfer into Cells," *Biophysical J.*, 63:1320–1327 (1992)), as enhanced uptake of a small, cotransported molecule was observed, but no long lasting effects were indicated, and the resistance across the cell membrane was not considered. In contrast, the present invention purposefully introduces molecules which are expected to cause long lasting cell membrane openings, in some cells of a tissue, thereby creating a long lasting diminished electrical resistance across the tissue for improved biopotential measurements.

Although this invention can be used with tissues in which the main source of electrical resistance is due to the resistance of the cell membranes of the cells of the tissue, it is preferred to use this invention with skin, a tissue that owes its electrical resistance mainly to the stratum corneum (SC). The SC is a dead tissue, containing no living cells. Instead, the resistance is due to approximately one hundred lipid bilayer membranes which are different in lipid composition from cell membrane composition. The fact that the SC is dead, and the resistance is very large, means that experimentation on isolated skin preparations are generally indicative of both in vitro and in vivo skin resistance behavior.

That is, it is well known that the main barrier of the skin to ionic and molecular transport is the stratum corneum (SC), and that the SC contains no living cells. Instead, the SC consists mainly of multilamellar bilayer membranes located between dead cell remnants, the corneocytes (see, for example, Goldsmith, "Physiology, Biochemistry, and Molecular Biology of the Skin, Second Edition," (NY: Oxford University Press) (1991)). For this reason, it is generally accepted that relevant and representative experimentation related to enhanced transport of ions and molecules can be carried out on skin preparations in vitro, and that the results of such in vitro experiments are predictive of the more-difficult-to-carry-out, and more expensive, in vivo experiments.

Thus, although the motivation and intent is to use this invention in vivo with living beings, the essential features of the invention can be adequately described by in vitro experimentation using skin preparations with areas of about 1 cm². The use of in vitro experimentation is also well established in transdermal drug delivery, because the main barrier to molecular transport is also the SC (see, for example, "Percutaneous Penetration Enhancers," Smith and Mailbach, Eds. (Boca Raton: CRC Press) (1995)). For this reason, in vitro experimentation on human skin is adequate to demonstrate the means for diminishing human skin resistance for the purpose of improving biopotential measurements.

In the case of skin where the main resistance is due to the SC, it is useful to employ resistance-decreasing agents that are long molecules with molecular weight greater than one kilodalton (MW>1000 gm/mol). In fact, it is particularly useful to employ long molecules whose length exceeds about 40 nm, in order to span the 5–6 bilayer membranes that separate adjacent corneocytes within the SC. Thus, for example, introduction of heparin molecules that exceed about 40 nm is believed to create long lasting aqueous pathway connections between adjacent corneocytes within a stack of corneocytes at the core of a local transport region (LTR), such that a long lasting resistance across the SC is achieved even though many of the electrically created aqueous pathways reseal (recover). Similarly, other long molecules such as long dextran molecules can be used.

The transtissue resistance can also be diminished by introducing a large quantity of small mobile ions from a solution of monovalent electrolytes (ionic species with charge $q=\pm e$), where $e=1.6\times10^{-19}$ C is the elementary electronic charge. For example, using a higher concentration of small ions in the tissue-contacting solution can lead to a decreased resistance following electroporation of the tissue. In this case, these ions serve as a resistance-decreasing agent. Long molecules which are polyvalent electrolytes (ionic species with charge magnitude $|q|>e$) can also serve as resistance-decreasing agents.

In another general embodiment of this invention, a keratin-disrupting agent is introduced into skin, such that at least one corneocyte within the stratum corneum (SC) is disrupted, leading to increased structural changes within the SC that involve partial opening of the SC, and therefore to a decreased electrical resistance across the skin. For example, an entire stack of corneocytes can become highly disrupted, and is the central core of a local transport region (LTR). In some cases, with introduction of modifying agents that disrupt keratin, this central LTR core is sufficiently disrupted that almost unhindered molecular transport occurs, as evidenced by the observation that a small molecule (sulforhodamine, 607 gm/mol) and a macromolecule (fluorescence-labeled lactalbumin, $\approx 15,000$ gm/mol) are then transported at almost the same rate, with the smaller sulforhodamine transported somewhat more. This relative lack of hindrance is consistent with an open structure, and therefore a large structural change. But if the structural change is large, it can be expected to have a long lifetime, and therefore the transport of the small ions responsible for $R_{skin}$ should be increased, thereby decreasing $R_{skin}$, and this decrease in $R_{skin}$ is therefore expected to have a long lifetime. For example, a suitable keratin-disrupting agent is a reducing agent. A more specific example is the use of sodium thiosulate as the reducing agent.

Throughout it is to be understood that although this invention emphasizes new means for decreasing transtissue resistance, the overall process is one of making an improved biopotential measurement. Thus, the process of this invention will usually involve the additional step of carrying out a biopotential measurement involving electrical currents across the tissue. This is particularly important for transdermal biopotential measurements such as ECG (EKG or electrocardiogram), in which the biopotential measurement is made cross skin. The decreased skin resistance is particularly valuable if biopotential measurements are made during exercise, and it therefore should be particularly useful for a cardiac stress test.

Other biopotential measurements which can be improved by the process of this invention include the EEG (electroencephalogram), the EMG (electromyogram), electrohysterographic measurements, electrokymographic measurements, biopotential measurements used in determining nerve impulse propagation speed, and in neural stimulation.

In noninvasive diagnostic measurements, such as noninvasive glucose measurement based on the response of peripheral nerves to stimulation, improved biopotential measurements may be useful, and thereby may lead to improved noninvasive measurements of glucose.

Although not previously mentioned here, it is to be understood that if transdermal biopotential measurement are involved, and the skin is not already hydrated (for example, by the occluding effect of placing an electrode that remains in place for about twenty minutes), then the additional step of ensuring that the skin is hydrated is employed.

To be useful, the decreased tissue resistance should be at low values for a time duration that is relevant to carrying out the associated biopotential measurement. Thus, the decreased tissue resistance should persist for about one second or more after ceasing pulsing that causes tissue electroporation, particularly in the case of transdermal biopotential measurements and the use of skin electroporation. In some cases, biopotential measurement times of ten or more minutes are desired, and in this case, then biopotential measurement is made at a time greater than one minute or more after ceasing pulsing that causes skin electroporation. In other cases, the biopotential measurement is made at a time greater than one hour after ceasing pulsing that causes skin electroporation, and in still other cases, the biopotential measurement is made at a time greater than ten hours after ceasing pulsing that causes skin electroporation.

EXAMPLES

Example 1

The first examples consist of transdermal resistance values obtained by pulsing human skin clamped in a side-by-side permeation chamber. The details of this type of experimental arrangement have been previously described for experiments aimed at demonstrating enhanced molecular transport across skin (se, for example, Prausnitz et al., "Transdermal Drug Delivery by Electroporation," Abstract, *Procced. Intern. Symp. Control. Rel. Bioact. Mater.* 19, Controlled Release Society, Orlando, Fla., July 26–29, pp. 232–233 (1992); Prausnitz et al., "Electroporation of Mammalian Skin: A Mechanism to Enhance Transdermal Drug Delivery," *Proc. Nat. Acad. Sci.,* 90:10504–10508 (1993); Pliquett et al., "Changes in the Passive Electrical Properties of Human Stratum Corneum due to Electroporation," *Biochem. Biophys. Acta,* 1239:111–121 (1995), Pliquett and Weaver, "Electroporation of Human Skin: Simultaneous Measurement of changes in the Transport of Two Fluorescent Molecules and in the Passive Electrical Properties," *Bioelectrochem. Bioenerget.,* 39:1–12 (1996)).

Table 1 gives the peak transdermal voltage ($U_{skin,0}$) in volts (V), the skin resistance, $R_{skin}$, in ohms ($\Omega$) during the pulse, the total electric charge in coulombs (C) transferred across the skin for the given protocol, the total electrical energy in joules (J) associated with dissipation within the skin for that pulsing protocol, and $R_{skin}$ after 2 h (two hours after pulsing ceased). These data are part of a larger data set from experiments that also involved studying molecular transport across the skin.

It is the postpulse $R_{skin}$ values that are relevant to the present invention, i.e. the $R_{skin}$ values 2 h after pulsing.

TABLE 1

| Applied Conditions | $U_{skin}$, 0 (V) | $R_{skin}$, during the pulse (Ω) | Q (Ω) | E (J) | $R_{skin}$, after 2 h (Ω) |
|---|---|---|---|---|---|
| 20 × (100 V-100 ms) | 43 | 454 | 0.12 | 3.13 | 18,000 |
|  | (41–45) | (415–490) | (0.11–0.25) | (2.94–3.27) | (14,000–34,500) |
| 20 × (100 V-300 ms) | 49 | 418 | 0.48 | 9.12 | 4410 |
|  | (40–58) |  | (0.43–0.50) | (8.99–11.2) | (4090–4730) |
| 20 × (200 V-100 ms) | 68 | 224 | 0.54 | 14.1 | 1500 |
| 20 × (200 V-300 ms) | 55 | 187 | 1.53 | 32.6 | 1560 |
|  | (48–62) | (166–208) | (1.40–1.67) | (28.2–37.0) |  |
| 20 × (300 V-100 ms) | 65 | 119 | 0.88 | 24.9 | 1500 |
|  | (63–68) | (114–124) | (0.85–0.92) | (24.1–25.7) | (1490–1510) |
| 20 × (300 V-300 ms) | 64 | 124 | 3.00 | 56.1 | 774 |
|  | (60–72) | (109–126) | (2.35–3.21) | (45.9–78.5) | (500–780) |
| 20 × (400 V-100 ms) | 77 | 98 | 1.32 | 27.1 | 1050 |
|  | (69–85) | (84–113) |  |  |  |
| 20 × (400 V-300 ms) | 71 | 112 | 4.25 | 62.8 | 840 |
|  | (68–96) | (85–136) | (2.52–4.46) | (18.5–96.3) | (180–1580) |
| 20 × (1000 V-1 ms) | 110 | 54 | 0.54 | 34.8 | 3940 |
|  | (99–127) | (40–86) |  |  |  |
| 720 × (1000 V-1 ms) |  |  | 2.21 | 207.9 | 1200 |
|  |  |  | (1.66–2.76) |  | (740–1650) |
| 240 × (1500 V-1 ms) | 100 | 34 | 0.84 | 53.16 | 290 |
|  | (76–156) | (24–78) | (0.81–0.87) | (43.2–63.12) | (130–450) |
| 720 × (1500 V-1 ms) |  |  | 1.89 | 78 |  |
|  |  |  | (1.54–2.24) | (56.4–99.6) |  |

The pulsing protocols for the data of Table 1 were as follows. For long pulse protocols, a cycle of 20 pulses was applied with a pulse spacing of 6 min (2 h total), the voltage applied at the electrodes was chosen to be in the range of 100 to 400 V. For the short pulse protocols, the voltage applied was either 1,000 or 1,500 V, and the number of pulses applied was either 240 or 720. The 240 pulses were applied with two values for the pulse spacing: for the first minute, 12 pulses were separated by 5 s, and then pulsing ceased for the next 5 min, with this six minute pattern repeated 20 times (2 h total). The 720 pulse protocols had all pulses spaced by a 5 s interval.

As shown in Table 1, in one experiment using short pulses, 2 hours after pulsing ceased an average value $R_{skin} \approx 290$ Ω was obtained for a pulsing protocol of 240 pulses, exponential pulses with time constant $\tau_p = 1$ ms, and 1500 V applied at electrodes distant from the skin, using side-by-side permeation chambers described previously (see Pliquett et al., "Changes in the Passive Electrical Properties of Human Stratum Corneum due to Electroporation," *Biochem. Biophys. Acta*, 1239:111–121 (1995); Pliquett and Weaver "Electroporation of Human Skin: Simultaneous Measurement of Changes in the Transport of Two Fluorescent Molecules and in the Passive Electrical Properties," *Bioelectrochem. Bioenerget.*, 39:1–12 (1996)). In Table 1, this pulsing protocol is indicated by an abbreviated notation, in this case 240×(1500 V–1 ms). Note that because of a variable voltage divider effect (Pliquett et al., 1995), the transdermal voltage was significantly smaller, approximately 100 V. In another experiment, using long pulses, 2 hours after pulsing ceased an average value $R_{skin} \approx 1050$ Ω was obtained for a pulsing protocol of 20 pulses, exponential pulses with time constant $\tau_p = 100$ ms, and 400 V applied at electrodes distant from the skin. In this case, the transdermal voltage maximum was about 77 V.

Example 2

Figure 2:
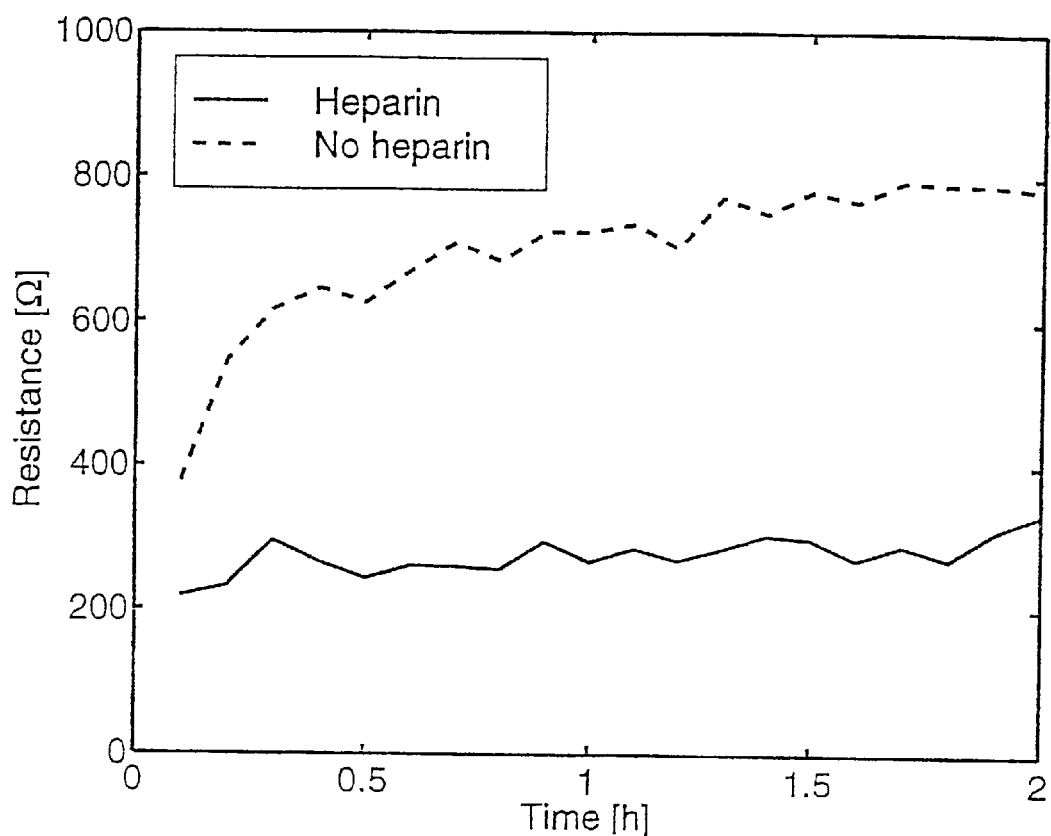
FIG. 2 is a plot of postpulse skin resistance with and without the use of heparin as a resistance-decreasing agent.

This experiment determined postpulse skin resistance with and without a long, linear charged molecule (heparin), which served as a resistance-decreasing agent that was introduced into aqueous pathways across the SC by electroporation. $R_{skin}$ was plotted over two hours postpulse and is shown in FIG. 2. The experimental conditions for this example are given below.

Skin preparation: Side-by-side permeation chambers held het stripped human epidermis, with an area $A_{skin} = 0.7$ cm$^2$ exposed to solution. This experimental apparatus has been described previously (see, for example, Pliquett and Weaver, "Electroporation of Human Skin: Simultaneous Measurement of Changes in the Transport of Two Fluorescent Molecules and in the Passive Electrical Properties," *Bioelectrochem. Bioenerget.*, 39:1–12 (1996)).

Heparin and fluorescent tracer molecules: The donor and receptor compartments are filled with phosphate-buffered saline (PBS; pH 7.4; 150 mM total salts, Sigma Chemical, St. Louis, Mo.). Sodium heparin ($\geq 140$ U/mg; Sigma Chemical) was provided in the donor compartment of the chamber, at concentrations from 0 200 mg/ml. Heparin is a class of molecules with a range of molecular weights (about 6,000 to 30,000 g/mol); the average MW of the heparin used in this study was about 20,000 g/mol. The estimated range of molecular lengths is about 30 to 140 nm. Heparin is composed of repeating units of glucosamine and either glucoronic or iduronic acid residues, and because each of these disaccharide units has from one to three sulfates, the molecule has a large negative charge. Two fluorescent water soluble molecules were also provided in the donor chamber, at a concentration of 1 mM: sulforhodamine (607 g/mol, charge=−1 e; red fluorescence) and calcein (623 g/mol; charge=−4 e; green fluorescence), so that the transport of molecules with nearly identical size but very different charge could be determined in a single skin preparation. The transport of calcein and sulforhodamine is believed to be irrelevant to the present invention, which deals with diminished skin resistance, but is mentioned for completeness.

HV Pulse application (electroporation), iontophoresis, and skin resistance measurement: High-voltage exponential pulses with peak amplitude of 1000 V and time constant $\tau_p = 1$ or 2 ms were applied through stainless steel electrodes at 5 s intervals for one hour (720 pulses). This is an experimental pulsing protocol used previously (see, for example, Prausnitz et al., "Electroporation of Mammalian Skin: A Mechanism to Enhance Transdermal Drug Delivery," Proc. Nat. Acad. Sci., 90:10504–10508 (1993)).

Iontophoresis conditions consisted of 1 mA/cm² for 1 hr. Skin electrical resistance, $R_{skin}$, was monitored as described previously (see Pliquett et al., "Changes in the Passive Electrical Properties of Human Stratum Corneum due to Electroporation," Biochem. Biophys. Acta, 1239:111–121 (1995)).

Estimation of the number of aqueous pathways per participating corneocyte: The "aqueous area," $A_W$, of a skin preparation is the effective area available for transport. Owing to Born energy and hindrance effects, this is not the total cross-sectional area of aqueous pathways, and is dependent on the molecule being transported. Similarly, the "fractional aqueous area" is $F_W = A_w/A_{skin}$. Previous experiments using similar pulsing conditions found $F_w \approx 6 \times 10^{-5}$ for calcein and sulforhodamine (see Pliquett and Weaver, "Electroporation of Human Skin: Simultaneous Measurement of Changes in the Transport of Two Fluorescent Molecules and in the Passive Electrical Properties," Bioelectrochem. Bioenerget., 39:1–12 (1996)). If transport were uniform across the skin preparation, then $F_w$ could be used to estimate the number of pathways per corneocyte. However, subsequent studies showed that molecular transport is concentrated within local transport regions (LTRs), and that all of the LTRs together occupy only a small fraction of $A_{skin}$, $f_{LTR} = A_{LTRs}/A_{skin} \approx 0.1$ or less (see Zewert et al., "Transport of DNA Antisense Oligonucleotides Across Human Skin by Electroporation," Biochem. Biophys. Res. Comm., 212:286–292 (1995); Pliquett et al., "Imaging of Fluorescent Molecule and Small Ion Transport through Human Stratum Corneum During High-Voltage Pulsing: Localized Transport Regions are Involved," J. Biophys. Chem., 58:185–204 (1996); Prausnitz et al., "Imaging Regions of Transport Across Human Stratum Corneum During High Voltage and Low Voltage Exposures," J. Pharm. Sci., 85:1363–1370 (1997)). Therefore, the fractional aqueous area within LTRs is $F_{W,LTR} = F_W/f_{LTR} \approx 6 \times 10^{-4}$. Electrically created pathways are believed to have radii $r_p \approx 1$ nm (see, for example, Weaver and Chizmandzhev, "Theory of Electroporation: A Review," Bioelectrochem. Bioenerget., 41:135–160 (1996)), so the number of aqueous pathways per corneocyte is estimated to be $N_p \approx F_{W,LTR} A_{cc}/(\Pi r_p^2) \approx 10^5$, where $A_{cc} \approx 5 \times 10^{-9}$ m² is the area of a corneocyte.

Example 3

This invention is also illustrated by experiments in which "modifying agents" were introduced into the stratum corneum (SC) by electroporation, with the "modifying agents" serving here as "resistance-decreasing agents." These experiments were carried out in side-by-side permeation chambers described previously (see Prausnitz et al., "Electroporation of Mammalian Skin: A Mechanism to Enhance Transdermal Drug Delivery," Proc. Nat. Acad. Sci., 90:10504–10508 (1993); Pliquett and Weaver, "Electroporation of Human Skin: Simultaneous Measurement of Changes in the Transport of Two Fluorescent Molecules and in the Passive Electrical Properties," Bioelectrochem. Bioenerget., 39:1–12 (1996)).

In some experiments, a pressure across the skin was applied by placing a pipette vertically in a top hole of the chamber, so that by adding a donor solution to the pipette a hydrostatic pressure of 0 to 10 cm water was applied. Both the prepulse and postpulse value of $R_{skin}$ was noted, with the postpulse skin resistance tending to remain at the value noted, which is after the completion of a pulsing protocol with many pulses.

In addition, several examples are given in which the "modifying agent" is a chemical reducing agent, which was provided in the donor compartment solution that contacts the SC. In Table 2 (below), several parameters were determined.

TABLE 2

| Expt. Index | Description | reducing agent | pulse len (msec) | pulse amp (V) | total time (hr) | temp. | pr. | flow thru | flow prot | pre-res (kΩ) | post-res (Ω) |
|---|---|---|---|---|---|---|---|---|---|---|---|
| 1031897 | pulsing control | | 1 | 1000 | 1 | room | | yes | no | 301 | 1235 |
| 2031897 | pulsing control | | 1 | 1000 | 1 | room | | yes | no | 358 | 1029 |
| 5020197 | control - no pulsing | 3M Na₂S₂O₃ | | | | 37° C. | | no | no | 48 | 46k |
| 2041097 | pulsing with pressure | | 1 | 1000 | 1 | room | 10 cm | yes | no | 716 | 804 |
| 2041497 | pulsing with pressure | | 1 | 1000 | 1 | room | 10 cm | yes | no | 580 | 959 |
| 3020697 | 0.01M red ag | 0.01 Na₂S₂O₃ | 1 | 1000 | 1 | 37° C. | | no | no | 159 | 564 |
| 2021397 | 0.1M red ag | 0.1 Na₂S₂O₃ | 1 | 1000 | 1 | 37° C. | | no | no | 43 | 157 |
| 1021997 | 1M red ag | 1M Na₂S₂O₃ | 1 | 1000 | 1 | room | | no | no | 50 | 1217 |
| 3013097 | 3M red ag | 3M Na₂S₂O₃ | 1 | 1000 | 1 | 37° C. | | no | no | 241 | 90 |
| 2042297 | pulsing with pressure and red ag | 3M Na₂S₂O₃ | 1 | 1000 | 1 | room | 7 cm | yes | no | 70 | 53 |
| 3041097 | pulsing with pressure and red ag | 3M Na₂S₂O₃ | 1 | 1000 | 1 | room | 8 cm | yes | no | 416 | 89 |
| 2030697 | pulsing with pressure and red ag | 3M Na₂S₂O₃ | 1 | 1000 | 1 | room | 10 cm | no | no | 132 | 191 |
| 1021897 | thioglycolic acid | 0.1M | 1 | 1000 | 1 | 37° C. | | no | no | 100 | 365 |
| 2021897 | dithiodiglycolic | 0.1M | 1 | 1000 | 1 | 37° C. | | no | no | 106 | 485 |

The notation "red ag" denotes the reducing agent most often used (sodium thiosulfate). As noted (bottom two rows), however, two other reducing agents were also used, "thioglycolic acid" (thioglycolic acid sodium; FW 114.1; Product #T0632, Sigma) and "dithiodiglycolic acid" (dithiodiglycolic acid; FW 182.2; Product #D5392, Sigma). Moreover, there are experiments with and without imposition of a pressure across the skin. The term "pulsing control" means that only electrical pulsing was used (no reducing agent was provided), with a protocol described previously in which 720 pulses were applied at 5 s intervals (spacing). In one case, a "control—no pulsing" is given, in which sodium thiosulfate ("$Na_2S_2O_3$") was provided at a high concentration (3M), but no high voltage pulses were applied, and this showed that sodium thiosulfate exposure alone caused an insignificant change in $R_{skin}$ (48 kΩ before exposure; 46 kΩ after exposure). Pulsing in the presence of a hydrostatically applied pressure difference ("pulsing with pressure") alone (rows 4 and 5), and pulsing in the presence of a hydrostatically applied pressure difference and sodium thiosulfate ("pulsing with pressure and red ag;" rows 10–12) are given. Pulsing with pressure and no reducing agent had postpulse $R_{skin}$ values slightly smaller (here 804 and 959 Ω) than typical pulsing with zero applied pressure (e.g. rows 1 and 2, with postpulse $R_{skin}$ of 1235 and 1029 Ω for these particular experiments).

Rows 6, 7 and 9 show a downward progression of postpulse $R_{skin}$ from 564 Ω to only 90 Ω at 37° C. as sodium thiosulfate concentration is increased from 0.01M to 3M, consistent with progressively greater alteration of the SC. Row 8 shows a room temperature (about 25° C.) result, for 1M sodium thiosulfate, and in this case the postpulse resistance was larger, 1217 Ω, consistent with lesser alteration of the SC. Rows 10–12 all involved the same high concentration of sodium thiosulfate, but slightly increasing pressure, and all of the postpulse resistance values were small (and suggest an upward trend).

The main feature of these data is that provision of a reducing agent with high voltage pulsing usually leads to significantly smaller postpulse $R_{skin}$ values than similar experiments without the reducing agent.

EQUIVALENTS

Those skilled in the art will recognize, or be able to ascertain using no more than routine experimentation, many equivalents to the specific embodiment of the invention described herein. Such equivalents are intended to be encompassed by the following claims.

What is claimed is:

1. A method for measuring a biopotential of an organism, comprising the steps of:
    a) electroporating a portion of a tissue surface of the organism; and
    b) measuring a biopotential of said organism with electrodes at the electroporated portion of the organism.

2. The method of claim 1 wherein the electroporating step a) is of a skin tissue surface.

3. The method of claim 2, wherein the measuring step b) is of the biopotential of a human.

4. The method of claim 2 wherein the biopotential measuring step is an electrocardiographic measurement.

5. The method of claim 4 wherein the electrocardiographic measuring step is made during exercise of the organism.

6. The method of claim 5 wherein the electrocardiographic measuring step is made during a cardiac stress test.

7. The method of claim 2 wherein the biopotential measuring step b) is an electroencephalographic measurement.

8. The method of claim 2 wherein the biopotential measuring step b) is an electromyographic measurement.

9. The method of claim 2 wherein the biopotential measuring step b) is an electrohysterographic measurement.

10. The method of claim 2 wherein the biopotential measuring step b) is an electrokymographic measurement.

11. The method of claim 2 wherein the biopotential measuring step b) is employed to measure nerve impulse propagation speed.

12. The method of claim 2 wherein the biopotential measuring step b) is employed in neural stimulation.

13. The method of claim 2 further including the step of hydrating the surface portion of the skin being electroporated.

14. The method of claim 2 wherein the biopotential measuring step b) is initiated at a time greater than about one second after electroporation of the skin surface.

15. The method of claim 2 wherein the biopotential measuring step b) is initiated at a time greater than about one minute after electroporation of the skin surface.

16. The method of claim 2 wherein the biopotential measuring step b) is initiated at a time greater than about one hour after electroporation of the skin surface.

17. The method of claim 2 wherein the biopotential measuring step b) is initiated at a time greater than about ten hours after electroporation of the skin surface.

18. The method of claim 1, further including the step of contacting said tissue surface with a resistance-decreasing agent, wherein said resistance-decreasing agent enters the electroporated tissue, thereby decreasing electrical resistance of the electroporated tissue.

19. The method of claim 18, wherein the electroporating step a) is of a skin tissue surface.

20. The method of claim 19, wherein the measuring step b) is of the biopotential of a human.

21. The method of claim 20, wherein contacting of the tissue surface is with a resistance-decreasing agent that is an elongate molecule having a molecular weight greater than about one kilodalton.

22. The method of claim 21, wherein the resistance-decreasing agent contacting the tissue surface is heparin.

23. The method of claim 22, wherein the resistance-decreasing agent contacting the tissue surface is dextran.

24. The method of claim 21, wherein the resistance-decreasing agent contacting the tissue surface is sufficiently elongate to span a bilayer membrane between corneocytes of stratum corneum of a skin tissue surface.

25. The method of claim 21, wherein the resistance-decreasing agent contacting the tissue surface is a monovalent electrolyte having an elementary electronic charge of about $1.6 \times 10^{-19}$ coulombs.

26. The method of claim 21, wherein the resistance-decreasing agent contacting the tissue surface is a polyvalent electrolyte.

27. The method of claim 21, further including the step of contacting the skin surface with a keratin-disrupting agent, whereby at least one corneocyte within stratum corneum of the skin tissue is disrupted, thereby increasing poration of the stratum corneum and decreasing electrical resistance of the skin tissue.

28. The method of claim 27, wherein the keratin-disrupting agent contacting the skin surface is a reducing agent.

29. The method of claim 28, wherein the reducing agent contacting the skin surface is sodium thiosulfate.

30. In a method for measuring a biopotential of an organism including the step of measuring the biopotential of said organism with electrodes at a tissue surface of organism:
    the improvement comprising electroporating said tissue surface prior to conducting said measurement.

* * * * *